(12) United States Patent
Fentem

(10) Patent No.: US 10,905,514 B2
(45) Date of Patent: Feb. 2, 2021

(54) SURGICAL DRAPE

(71) Applicant: Susan Kay Fentem, Moline, IL (US)

(72) Inventor: Susan Kay Fentem, Moline, IL (US)

( * ) Notice: Subject to any disclaimer, the term of this patent is extended or adjusted under 35 U.S.C. 154(b) by 0 days.

(21) Appl. No.: 16/851,861

(22) Filed: Apr. 17, 2020

(65) Prior Publication Data

US 2020/0337793 A1 Oct. 29, 2020

Related U.S. Application Data

(60) Provisional application No. 62/839,573, filed on Apr. 26, 2019.

(51) Int. Cl.
*A61B 46/20* (2016.01)
*A61B 46/00* (2016.01)

(52) U.S. Cl.
CPC .............. *A61B 46/20* (2016.02); *A61B 46/30* (2016.02); *A61B 2046/201* (2016.02)

(58) Field of Classification Search
CPC ......... A61B 46/00; A61B 46/20; A61B 46/30; A61B 2046/201; A61B 46/10; A61B 46/23; A61B 46/40; A61B 2046/205; A61B 2046/234; A61B 2046/236
USPC ........................................................ 128/856
See application file for complete search history.

(56) References Cited

U.S. PATENT DOCUMENTS

| | | | | |
|---|---|---|---|---|
| 4,976,274 | A * | 12/1990 | Hanssen ................ | A61B 46/23 128/849 |
| 8,863,747 | B1 * | 10/2014 | Stephenson ............ | A61B 46/00 128/854 |
| 2006/0219249 | A1 * | 10/2006 | Czajka .................... | A61B 46/00 128/849 |
| 2008/0283064 | A1 * | 11/2008 | Block ..................... | A61B 46/00 128/853 |
| 2011/0174316 | A1 * | 7/2011 | Czop ...................... | A61B 46/00 128/849 |
| 2012/0298115 | A1 * | 11/2012 | Haines ................... | A61B 46/00 128/852 |
| 2012/0312308 | A1 * | 12/2012 | Allen ...................... | A61B 46/00 128/853 |
| 2013/0104909 | A1 * | 5/2013 | Barrier ................... | A61B 46/30 128/852 |
| 2017/0258544 | A1 * | 9/2017 | Osman ...................... | A61F 7/00 |
| 2019/0053867 | A1 * | 2/2019 | Stamm ................... | A61B 46/20 |
| 2019/0216565 | A1 * | 7/2019 | Menut .................... | A61B 46/20 |

* cited by examiner

*Primary Examiner* — Kari K Rodriquez
(74) *Attorney, Agent, or Firm* — Hamilton IP Law, PC; Jay R. Hamilton; Charles A. Damschen

(57) ABSTRACT

A surgical drape may be configured for use with a patient positioning table for an anterior approach hip surgical procedure. In at least one illustrative embodiment the surgical drape may be specifically configured for use with an anterior approach hip total replacement surgery. The surgical drape is configured with an aperture that provides access to a patient's surgical site, which aperture may be generally rectangular-shaped in one illustrative embodiment. The aperture may be centered between a right and left edge of the surgical drape such that one configuration of the surgical drape may be used for an anterior approach hip surgical procedure of either a patient's left or right hip.

18 Claims, 6 Drawing Sheets

SURGICAL DRAPE

CROSS REFERENCE TO RELATED APPLICATIONS

This non-provisional utility patent application claims the filing benefit of provisional U.S. Pat. App. No. 62/839,573 filed on Apr. 26, 2019, which application is incorporated by reference herein in its entirety.

FIELD OF THE INVENTION

The present disclosure relates to a surgical drape, and more specifically a surgical drape configured for use with an anterior approach hip surgical procedure.

STATEMENT REGARDING FEDERALLY SPONSORED RESEARCH OR DEVELOPMENT

No federal funds were used to develop or create the invention disclosed and described in the patent application.

REFERENCE TO SEQUENCE LISTING, A TABLE, OR A COMPUTER PROGRAM LISTING COMPACT DISK APPENDIX

Not Applicable.

AUTHORIZATION PURSUANT TO 37 C.F.R. § 1.171 (d)(c)

A portion of the disclosure of this patent document may contain material that is subject to copyright and trademark protection. The copyright owner has no objection to the facsimile reproduction by anyone of the patent document or the patent disclosure, as it appears in the Patent and Trademark Office patent file or records, but otherwise reserves all copyrights whatsoever.

BACKGROUND—ANTERIOR APPROACH HIP SURGICAL PROCEDURE

A total hip replacement is a type of surgical procedure also referred to as total hip arthroplasty. This procedure replaces the hip joint with artificial components. An orthopedic surgeon can do this procedure in a lateral position (on the patient's side), which is the traditional approach or in a supine position (on the patient's back), which is the anterior approach. Total hip arthroplasty with the anterior approach is of particular relevance to this disclosure). This anterior approach surgery may also be called mini, modified, minimally invasive, or muscle-sparing surgery.

The hip is a ball-and-socket joint. The thighbone (femur) bends inward near the hip. The upper end (femoral head) has a round shape. The femoral neck bends inward. The femoral shaft is the long straight bone. The head of the femur fits into a cup-shaped cavity. This cavity is called the acetabulum. A flexible and tough protective tissue called cartilage covers the inside of the acetabulum and the femoral head. Tissue lining the joint produces fluid that with the cartilage helps the bones move easily against each other. The muscles and ligaments (strong fibrous tissues) hold the joint together.

An orthopedic surgeon can do hip replacement surgery to replace a damaged hip joint due to arthritis or degenerative joint disease. This surgery can ease pain and helps improve movement. During the surgery, the surgeon will replace the hip joint with artificial implants. The artificial implants can be metal or ceramic, or a combination of these. It may have a lining made of plastic, metal, or ceramic. Using the anterior approach allows the surgeon to perform the surgery through a smaller surgical cut (incision). The incision is made in the front of the hip rather than in the side or back, which would be in traditional hip replacements. Other advantages of an anterior approach procedure include: (1) less muscle trauma; (2) less pain; (3) earlier and easier recovery; (4) decreased limping; (5) shorter hospital stay; (6) decreased chance of hip dislocations; (7) decreased operative time; (8) potential decreased blood loss due to smaller incision; and/or, (9) potential decrease in infection due to smaller incision This surgery is performed under regional (spinal) anesthesia or general anesthesia. To improve the surgical procedure outcome, it is important to maintain a sterile surgical space (known as the sterile field) particularly around the equipment and the patient. The prior art surgical drape has several undesirable features and disadvantages, including but not limited to the prior art surgical drapes being incorrectly sized and shaped so that they are not long enough and cannot provide adequate coverage that is needed to provide complete coverage of the patient during draping.

BRIEF DESCRIPTION OF DRAWINGS

The accompanying drawings, which are incorporated in and constitute a part of this specification, illustrate embodiments and together with the description, serve to explain the principles of the methods and systems.

Figure 1A:
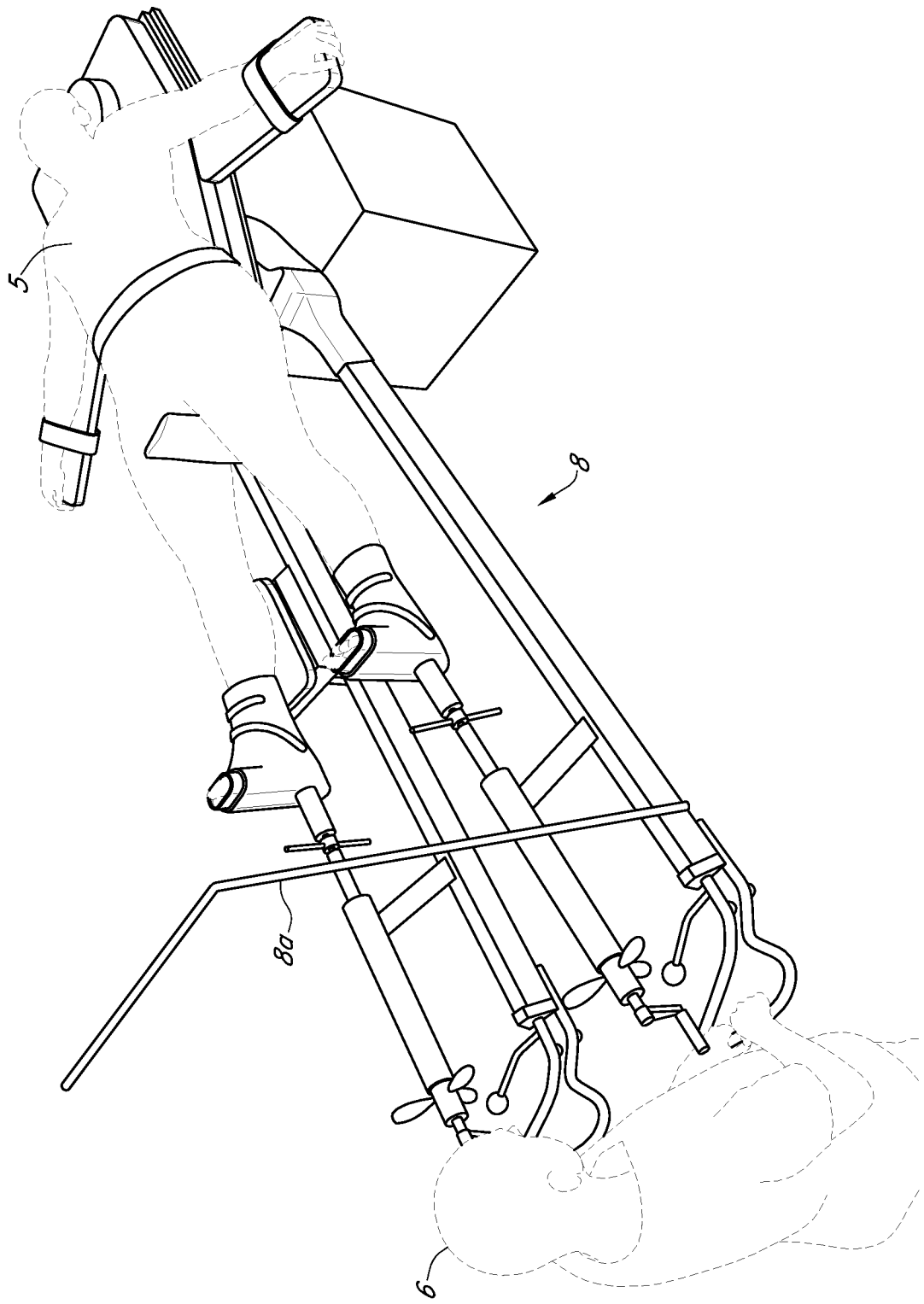
FIG. 1A is a perspective view of a patient positioning table which can be used with the surgical drape of the present disclosure.

| DETAILED DESCRIPTION - LISTING OF ELEMENTS | |
|---|---|
| Element Description | Element Number |
| Patient | 5 |
| Medical personnel | 6 |
| Patient positioning table | 8 |
| Table bar | 8a |
| Surgical drape | 10 |
| Head end | 12 |
| Left edge | 13 |
| Bar end | 14 |
| Right edge | 15 |
| Aperture | 16 |
| Armboard cover | 20 |
| Pleat | 22 |

DETAILED DESCRIPTION OF INVENTION

Before the present methods and apparatuses are disclosed and described, it is to be understood that the methods and apparatuses are not limited to specific methods, specific components, or to particular implementations. It is also to be understood that the terminology used herein is for the purpose of describing particular embodiments/aspects only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

"Aspect" when referring to a method, apparatus, and/or component thereof does not mean that limitation, functionality, component etc. referred to as an aspect is required, but rather that it is one part of a particular illustrative disclosure and not limiting to the scope of the method, apparatus, and/or component thereof unless so indicated in the following claims.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and apparatuses. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and apparatuses. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and apparatuses may be understood more readily by reference to the following detailed description of preferred aspects and the examples included therein and to the Figures and their previous and following description. Corresponding terms may be used interchangeably when referring to generalities of configuration and/or corresponding components, aspects, features, functionality, methods and/or materials of construction, etc. those terms.

It is to be understood that the disclosure is not limited in its application to the details of construction and the arrangements of components set forth in the following description or illustrated in the drawings. The present disclosure is capable of other embodiments and of being practiced or of being carried out in various ways. Also, it is to be understood that phraseology and terminology used herein with reference to device or element orientation (such as, for example, terms like "front", "back", "up", "down", "top", "bottom", and the like) are only used to simplify description, and do not alone indicate or imply that the device or element referred to must have a particular orientation. In addition, terms such as "first", "second", and "third" are used herein and in the appended claims for purposes of description and are not intended to indicate or imply relative importance or significance.

The following detailed description is of the best currently contemplated modes of carrying out illustrative embodiments of the present disclosure. The description is not to be taken in a limiting sense but is made merely for the purpose of illustrating the general principles of the present disclosure, since the scope of the invention is best defined by the appending claims. Various inventive features are described below herein that can each be used independently of one another or in combination with other features.

Disclosed herein are components that can be used with at least one embodiment of a surgical drape 10. It is understood that when combinations, subsets, interactions, groups, etc. of these components are disclosed, and that while specific reference of each various individual and collective combinations and permutation of these may not be explicitly disclosed, each is specifically contemplated and described herein, for all potential embodiments of the surgical drape 10. This applies to all aspects of this application including, but not limited to, components of a surgical drape 10 and methods for using same. Thus, if there are a variety of additional components that can be added it is understood that each of these additional components can be added with any specific embodiment or combination of embodiments of the surgical drape 10 and/or methods of using same. The surgical drape 10 and methods of using same may be understood more readily by reference to the following detailed description of preferred embodiments and the examples included therein and to the Figures and their previous and following description.

ILLUSTRATIVE EMBODIMENT AND METHOD OF USE

The surgical drape 10 pictured and described herein may be effective at maintaining a sterile space around the patient as it is correctly sized for an anterior approach hip surgical procedure (which surgical procedure includes but is not limited to a hip replacement unless otherwise indicated in the following claims) and an aperture 16 properly positioned within the periphery of the surgical drape 10 such that the patient to be properly positioned for the procedure and medical personnel may adequately access the patient. Although the Background Section herein provides details related to one specific hip surgical procedure (i.e., hip replacement), the surgical drape 10 as disclosed herein is not limited to hip replacements and may be utilized for any anterior approach hip surgical procedure without limitation unless otherwise indicated in the following claims. The surgical drape 10 disclosed herein may mitigate and/or eliminate at least one, a combination, or all of the disadvantages of the prior art surgical drapes. Accordingly, the surgical drape 10 disclosed herein may allow for a sterile space, proper patience positioning for the procedure, and improved access by medical personnel for monitoring the patient, providing medicine and/or anesthesia, and managing the patient's 5 position during the procedure, without restriction and limitation unless otherwise indicated in the following claims.

Figure 1B:
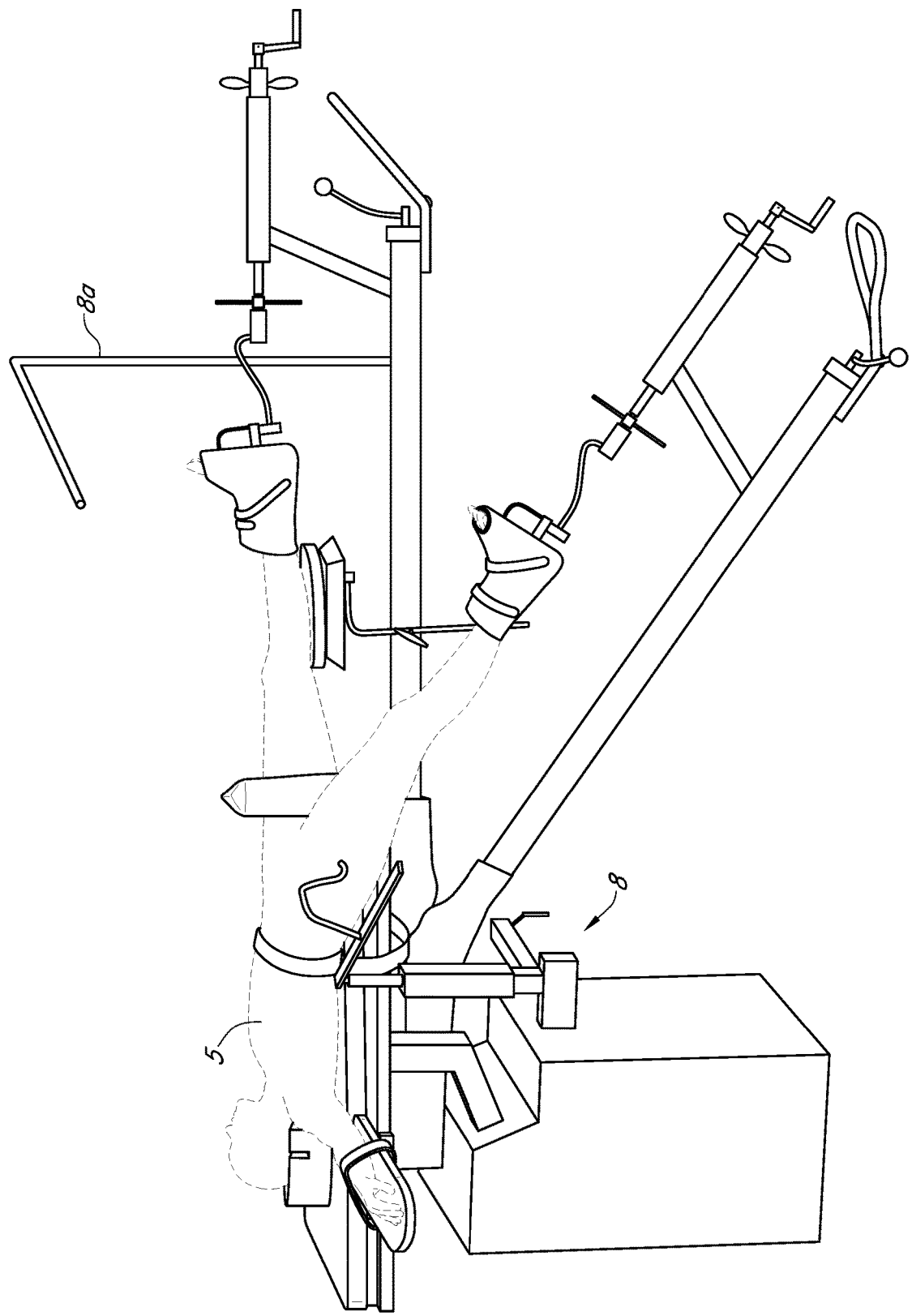
FIG. 1B is another perspective view of a patient positioning table which can be used with the surgical drape of the present disclosure.

Referring now to FIGS. 1A & 1B, shown therein in perspective view is a patient positioning table 8. The specific patient positioning table 8 shown in FIGS. 1A & 1B is a Hana® Table, which may be designed to enable a surgeon to perform hip replacement surgery using an anterior approach, wherein the patient 5 is laying supping (i.e., on their back) as shown in FIGS. 1A & 1B. One or more table bars 8a may extend upward from the main platform of the patient positioning table 8, the table bar 8a may serve to elevate the surgical drape 10 such that medical personnel 6 may access a portion of the patient 5 and/or patient positioning table 8 during use of the surgical drape 10 as described in further detail below. Although the surgical drape 10 is shown and described herein with reference to a patient positioning table 8 configured as a Hana® Table, the scope of the surgical drape 10 and/or method of using same are not so limited unless otherwise indicated in the following claims.

Figure 2:
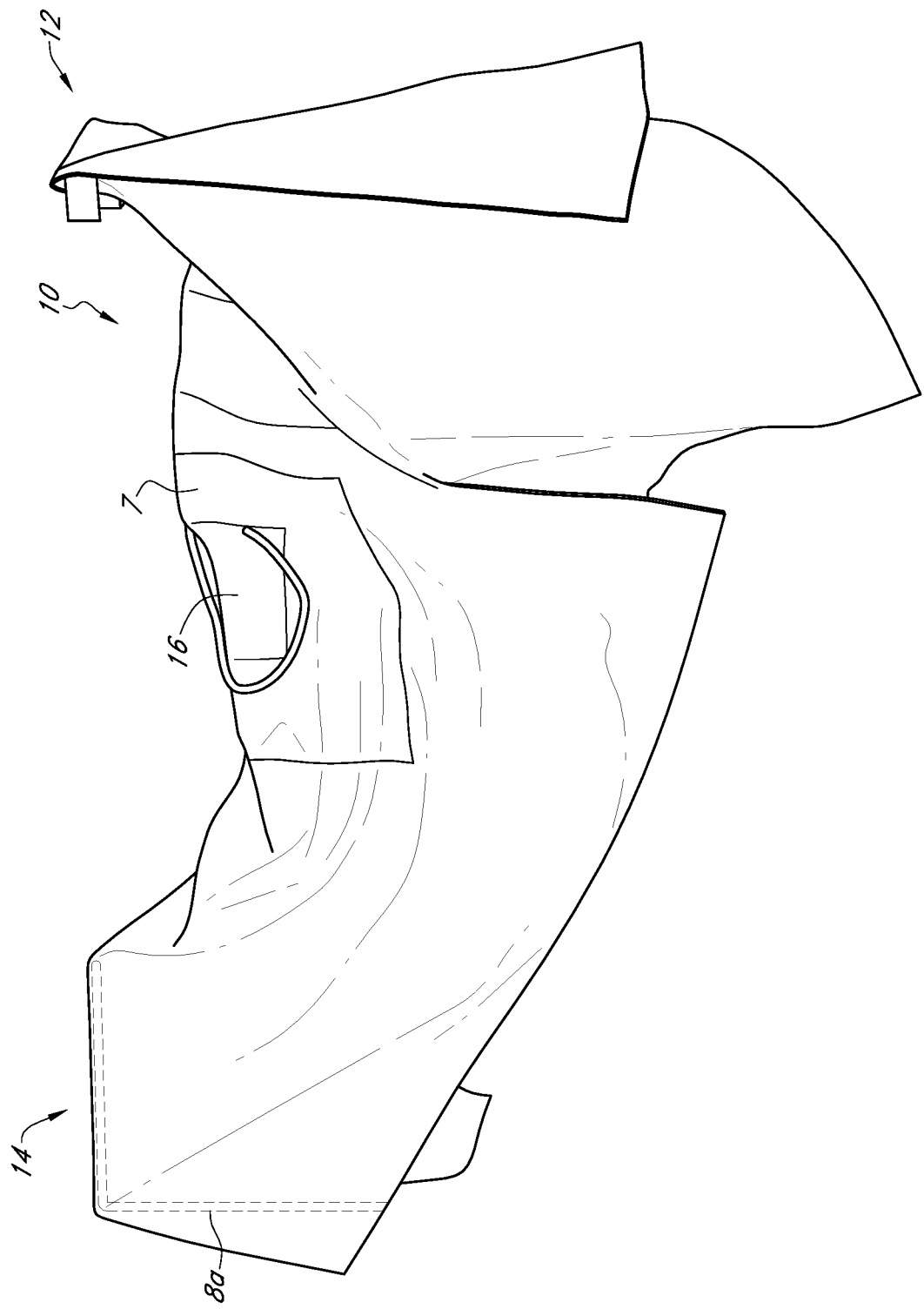
FIG. 2 provides a side perspective view of an illustrative embodiment of a surgical drape with a patient positioned under the surgical drape, wherein the patient may be positioned on a patient positioning table such as that shown in FIGS. 1A & 1B.

Referring now primarily to FIG. 2, therein is provided a perspective view of the illustrative embodiment of a surgical drape 10 positioned over a patient 5 positioned on the patient positioning table 8 of FIGS. 1A & 1B. As shown herein, the surgical drape 10 may be configured such that it adequately separates the patient from an external environment and/or provides a barrier for contaminants to and/or from the surgical site. Generally, the surgical drape 10 may be configured as a sheet-like, flexible cover to be used with certain surgical procedures so as to at least maintain sterility of the surgical site, prevent egress of bodily fluids, and/or prevent ingress of contaminants. In this manner, the surgical drape 10 may serve to create a barrier to a sterile field on a first side of the surgical drape 10 (which in at least one illustrative embodiment is the side facing away from the patient) and allow access to a patient and/or portion of a patient on an opposite side of the surgical drape 10 (which in at least one illustrative embodiment is the side facing toward the patient). In the illustrative embodiments of the surgical drape 10 pictured herein, the surgical drape 10 may have an area sufficient to cover the entirety of a patient's 5 body (for a relatively high percentage of anthropometries for adults) during an anterior approach hip surgical procedure, even when the patient's 5 arms and legs are fully extended outward from the patient's 5 body (e.g., in a position the same as or similar to that shown in FIGS. 1A & 1B).

Figure 3A:
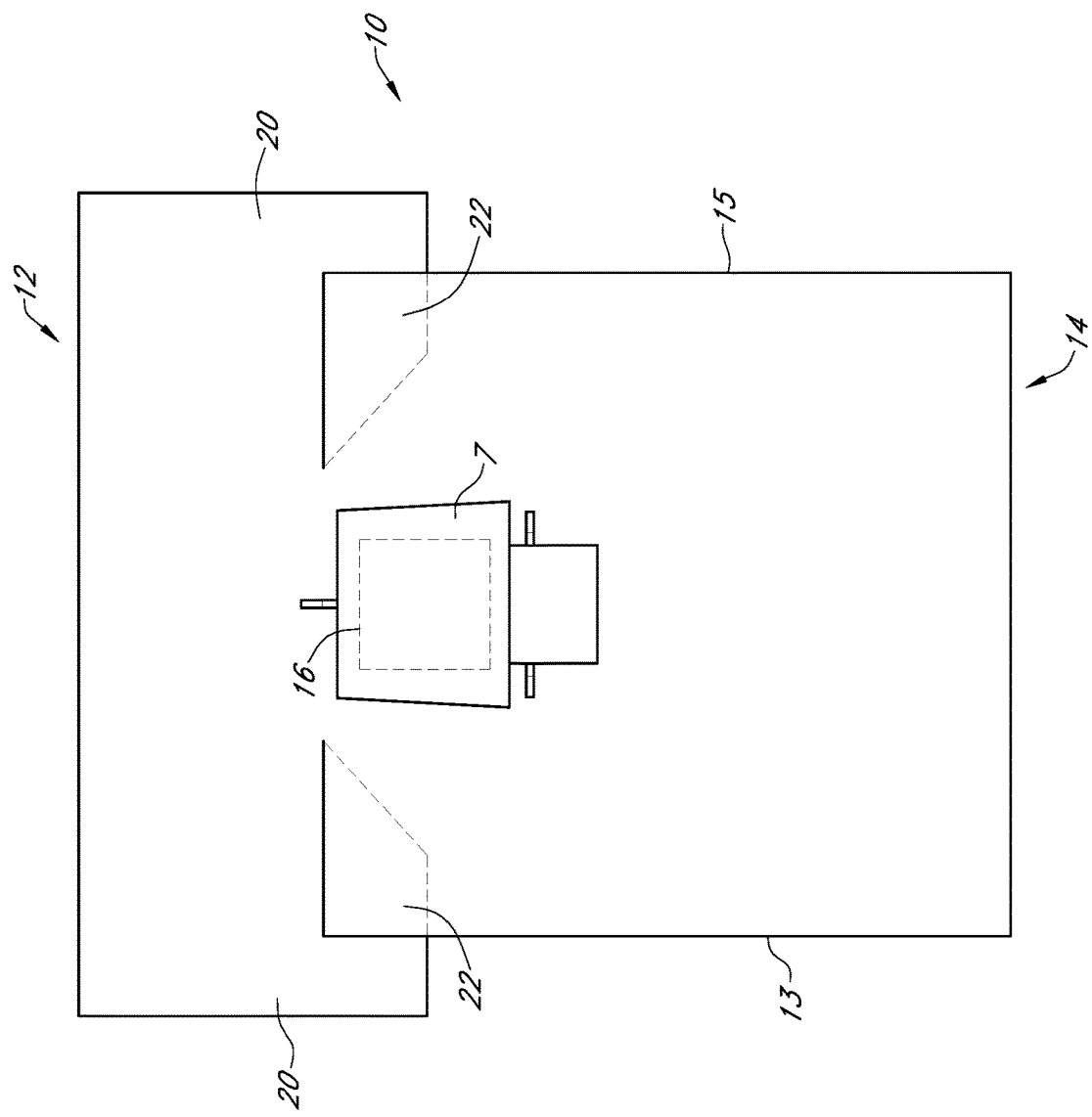
FIG. 3A is a detailed front view of the illustrative embodiment of the surgical drape shown in FIG. 2.
Figure 3B:
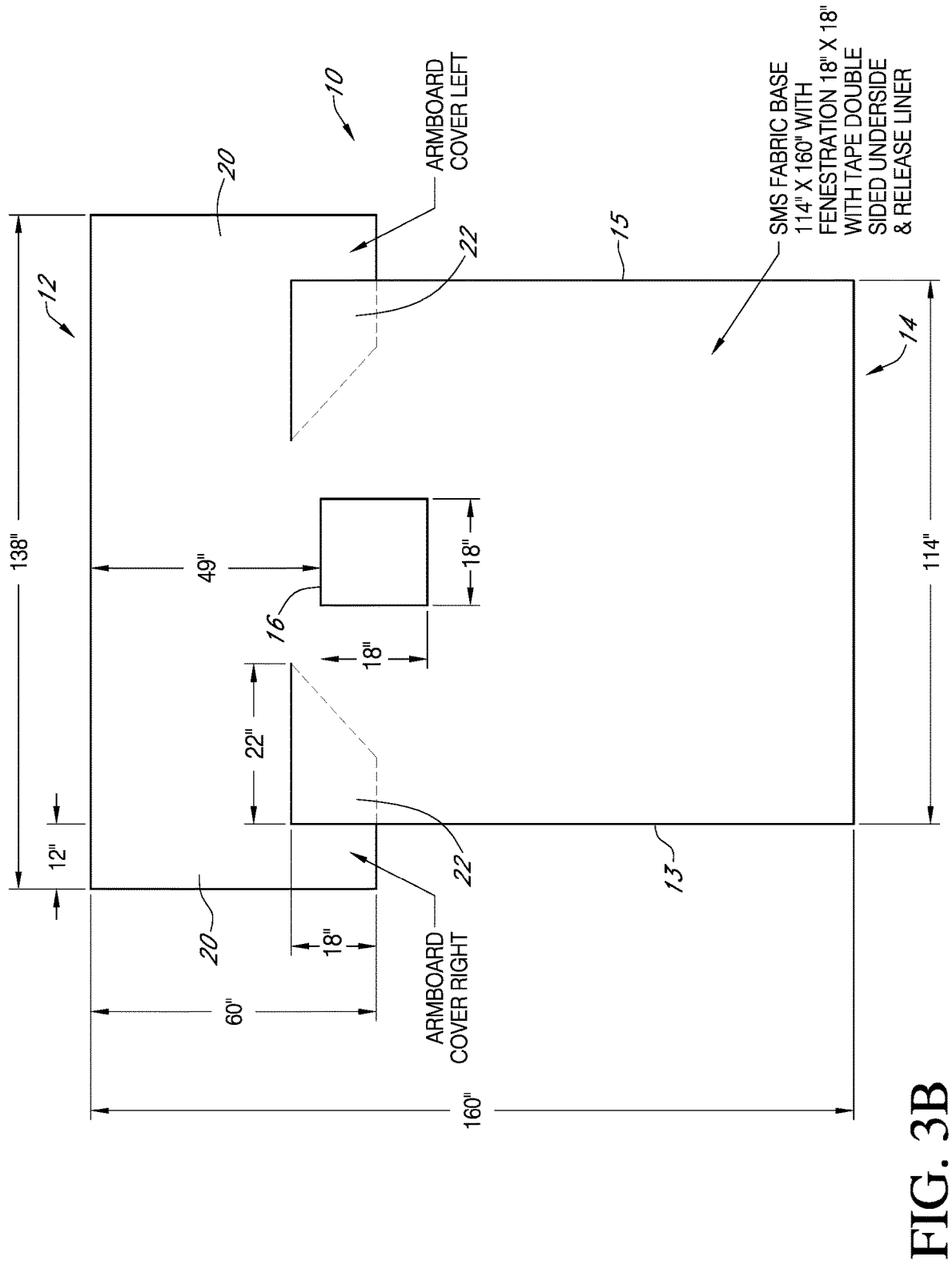
FIG. 3B is a detailed front view of the illustrative embodiment of the surgical drape of FIG. 3A, wherein various illustrative dimensions are shown.

Front (i.e., exterior with respect to a patient 5) views of the illustrative embodiment of a surgical drape 10 are shown in FIGS. 3A & 3B, wherein dimensions of various features of the surgical drape 10 are provided in FIG. 3B. Generally, the surgical drape 10 may comprised a head end 12 and a bar end 14 that are opposite one another as well as a left edge 13 and a right edge 15 also opposite one another. The left edge 13 and right edge 15 may be generally parallel with one another and generally perpendicular with respect to the head end 12 and bar end 14.

The illustrative embodiment of the surgical drape 10 may be formed with an armboard cover 20 on either edge 13, 15, thereof adjacent the head end 12. The armboard cover 20 may cooperate with a pleat 22 as shown by the hidden lines in FIGS. 3A & 3B (which represent folded edges of the material comprising the pleat 22) to provide additional coverage for the surgical drape 10 as needed. Other embodiments of a surgical drape 10 may have differently configured armboard covers 20 and/or pleats 22 (i.e., different dimensions, positions, etc.) without limitation unless otherwise indicated in the following claims.

As shown in FIG. 3B, the length of the surgical drape 10 (i.e., the distance from the head end 12 to the bar end 14) may be 160 inches. In other illustrative embodiments the length of the surgical drape may be 155, 154, 150, 148, 145, 144, 140, 136, 135, or 130 inches in length. It is contemplated that such a length may allow an operator of the patient positioning table 8, which operator may be manipulating the controls of same to properly position the patient and/or portion of the patient, to adequately access the controls for the patient positioning table 8 without entering the sterile field for the surgical procedure. During one illustrative method of use, it is contemplated that the head end 12 may be engaged with a pole or bar on either edge 13, 15 (which pole may be configured as an IV pole or bar) to create a barrier for the sterile field adjacent the patient's 5 head and/or torso even with the patient's 5 arms fully extended outward from the patient's 5 torso (e.g., in a position the same as or similar to that shown in FIGS. 1A & 1B), thereby providing medical personnel 6 access to the patient's 5 arms as needed (e.g., for IV placement, manipulation, placement, or medication delivery, placement of patient 5 monitoring equipment and/or sensors, etc.) without the medical personnel 6 entering the sterile field. The bar end 14 may be positioned over one or more table bars 8a opposite the head end 16 to create a barrier for the sterile field adjacent the patient's 5 feet even with the patient's 5 legs fully extended (e.g., in a position the same as or similar to that shown in FIGS. 1A & 1B) such that medical personnel 6 may access the controls of the patient positioning table 8 adjacent the bar end 14 without the medical personnel 6 entering the sterile field. However, other methods of using the surgical drape 10 exist and the scope of the present disclosure is not limited by the specific structures and/or methods used to engage either the head end 12 or bar end 14 of the surgical drape 10 disclosed herein unless otherwise indicated in the following claims.

The surgical drape 10 may include an aperture 16 positioned on an interior portion thereof. Generally, the aperture 16 may be positioned between the edges 13, 15 of the surgical drape 10 such that the surgical drape 10 is generally symmetrical in at least one dimension, i.e., the dimension parallel to the left and right edges 13, 15. Further, the aperture 16 may be positioned closer to the head end 12 than the bar end 14. As shown in FIG. 3B, the top edge of the aperture 16 may be located between 40 and 50 inches from the top edge of the head end 12 of the surgical drape 10 (and in the illustrative embodiment is shown located 49 inches from the edge of the head end 12 thereof). Such a symmetrical configuration of the aperture 16 with respect to the edges 13, 15 may allow the surgical drape 10 to be used for either a right hip or left hip of a patient 5 during an anterior approach hip surgery, such as a hip replacement without limitation unless otherwise indicated in the following claims. However, the optimal position of the aperture 16 with respect to the head end 12 and bar end 14 may vary depending on the specific application of the surgical drape 10 and in other illustrative embodiments is 60, 56, 55, 52, 50, 48, 45, 44, 40, 36, 35, or 30 inches from the edge of the head end 12 and is therefore in no way limiting to the scope of the surgical drape 10 unless otherwise indicated in the following claims.

In the illustrative embodiment pictured herein, the aperture 16 may be configured to have a rectangular shape. In other illustrative embodiments the shape of the aperture 16 may be square in shape, and in still other illustrative embodiments the shape may be curved, such as circular, ellipse, oval, or ovoid (a combination of curved and straight sides) without limitation unless otherwise indicated in the following claims.

The optimal dimensions of the aperture 16 may vary from one application of the surgical drape 10 (and/or method of using same) to the next, and are therefore in no way limiting to the scope of the present disclosure unless otherwise indicated in the following claims. In the illustrative embodiment pictured herein, the aperture 16 may configured as an 18-inch-by-18-inch square, but the scope of the present disclosure is not so limited unless otherwise indicated in the following claims. In another illustrative embodiment the aperture may be a 15-inch by 20-inch rectangle, and it is contemplated that the optimal shape and size of the aperture 16 may vary from one application of the surgical drape 10 to the next. In still other embodiments the aperture 16 may be configured as a circle having a diameter of 24, 22, 20, 18, 16, 14, or 12 inches. Accordingly, the specific configuration of the aperture (e.g., the shape, dimensions, etc.) in no way limits the scope of the present disclosure unless otherwise indicated in the following claims.

In one method of use, a barrier drape 7 and/or collection pouch may be positioned around the aperture 16 to further mitigate and/or prevent unwanted ingress of contaminants to the surgical site and/or egress of other materials from the surgical site. In one illustrative embodiment the barrier drape 7 may be configured as a 3M Ioban 2 Antimicrobial Incise Drape. However, any suitable barrier drape 7 may be used without limitation unless otherwise indicated in the following claims, and the optimal barrier drape 7 may vary from one application of the surgical drape 10 to the next. Additionally, it is contemplated that for certain applications a barrier drape 7 may not be required. Accordingly, the scope of the surgical drape 10 as disclosed herein is not limited by the presence or absence of a barrier drape 7 unless otherwise indicated in the following claims.

Figure 4:
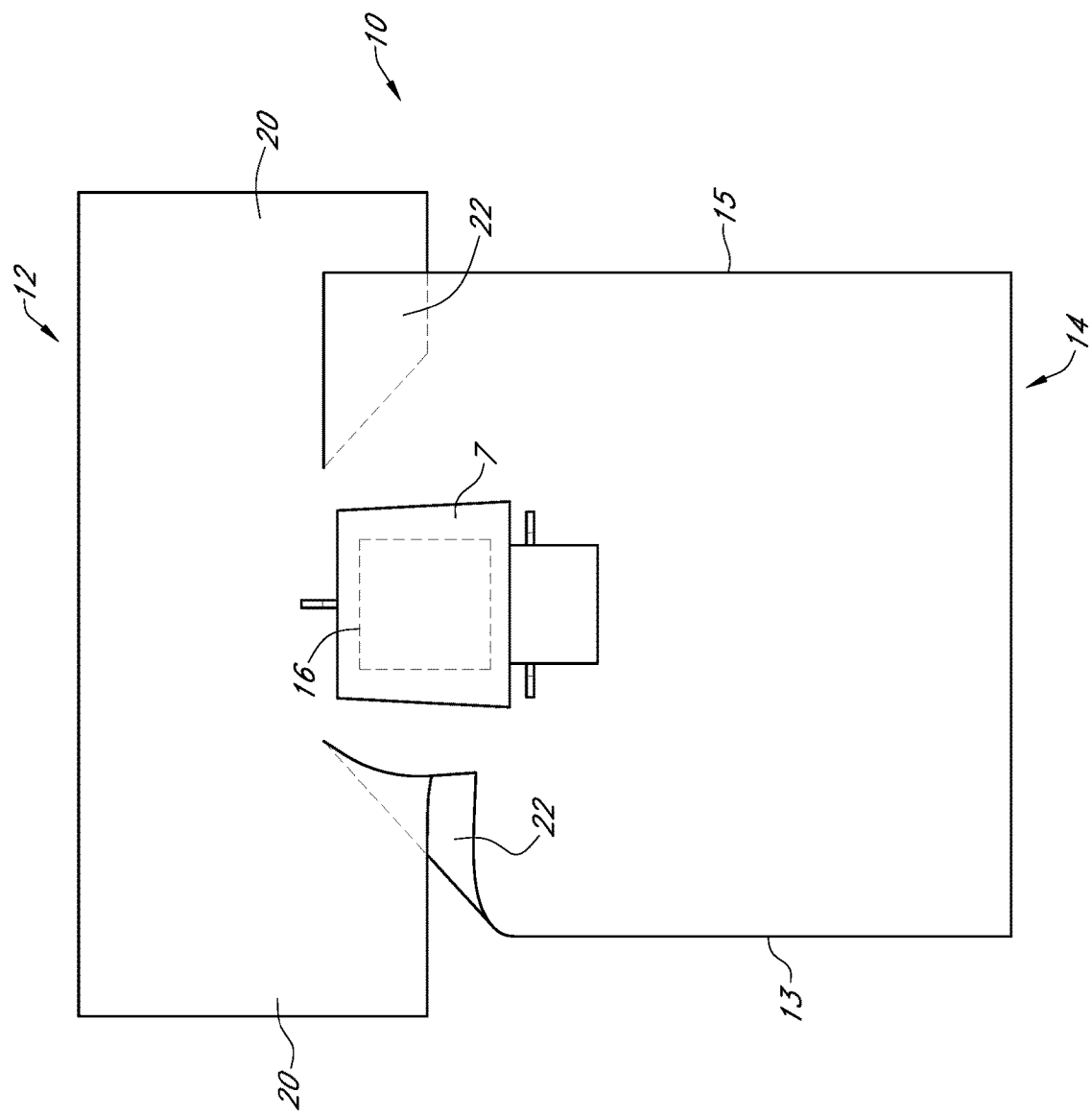
FIG. 4 is a detailed front view of the surgical drape shown in FIGS. 2, 3A, & 3B at the right armboard cover and associated pleat (which may be adjacent the patient's right arm during use), where a portion of the left edge has been folded over to reveal a portion of the associated pleat.

Referring now generally to FIGS. 3B & 4, the illustrative embodiment of a surgical drape 10 may be configured an armboard cover 20 on both the left and right edges 13, 15 adjacent the head end 12. The armboard covers 20 may provide increased coverage over an area of an patient adjacent the patient's 5 head and/or torso, such that the patient's 5 arms may be extended (e.g., in a position the same as or similar to that shown in FIGS. 1A & 1B) during an anterior approach hip surgical procedure but simultaneously be sufficiently covered by the surgical drape 10 so as to maintain the appropriate level of sterility for the patient 5. The increased width adjacent the armboard covers 20 provides continuous sterility along the width of the surgical drape 10 even when the patient's 5 arms are extended (e.g., in a position the same as or similar to that shown in FIGS. 1A & 1B) such that medical personnel (e.g., an anesthesiologist, anesthetist, etc.) may access the patient's 5 arms, intravenous equipment, patient 5 monitoring equipment and/or sensors, etc. without limitation unless otherwise indicated in the following claims.

As shown, additional fabric comprised of a pleat 22 may be used to provide additional coverage at either armboard cover 20. It is contemplated that this pleat 22 may be folded flat as shown in FIGS. 3A & 3B, wherein the hidden lines represent the folded edges of the material comprising the pleat(s) 22, but may be expanded as necessary during use to extend a portion of the surgical drape 10 to the desired position. The pleat 22 is shown expanded in FIG. 4, wherein a portion of the left edge 13 has been folded over toward the right edge 15 such that the entire bottom edge of the associated armboard cover 20 is shown, and the top surface of the pleat 22 that is visible in FIGS. 3A & 3B is now hidden. Generally, the optimal configuration of the pleat 22 and/or position thereof for a specific application may vary without limitation unless otherwise indicated in the following claims. For at least one application, namely an anterior approach hip replacement surgery, it is contemplated that the dimensions shown in FIG. 3B may be especially advantageous.

Referring now to FIG. 3B, which provides various dimensions for an illustrative embodiment of a surgical drape 10, the length thereof (i.e., the dimension from the edge at the head end 12 to the edge at the bar end 14) may be 160 inches. The width at the bar end 14 (i.e., the dimension from the left edge 13 to the right edge 15 at the bar end 14) may be 114 inches. In other illustrative embodiments the width at the bar end may be 112, 106, 100, 96, 94, 90, 84, 80, or 78 inches. The width at the head end 12 with the armboard covers 20 extended may be 138 inches, such that each armboard cover 20 may account for 12 inches of overall width. In other illustrative embodiments each armboard cover 20 may account for 10, 8, or 6 inches of overall width. The armboard covers 20 may extend from the terminal edge at the head end 12 toward the bar end 14 a distance of from 24 to 72 inches, and more preferably by a distance of 60 inches as shown in FIG. 3B. In other illustrative embodiments the armboard covers 20 may extend from the terminal edge at the head end 12 a distance of 30, 36, 42, 48, 54, 66, or 78 inches. The optimal configuration (e.g., dimensions, shape, etc.) of the armboard covers 20 may vary from one application of the surgical drape 10 to the next and is therefore in no way limiting to the scope of the present disclosure unless otherwise indicated in the following claims.

The pleat 22 may be configured such that the dimension of the pleat 22 parallel to the left and right edges 13, 15 may be 18 inches and the dimension of the pleat 22 parallel to the edge on the head end 12 and bar end 14 may be 22 inches. Additionally, the pleat 22 may be configured such that a fold therein (shown at least in FIGS. 3A, 3B, & 4) includes a vertex. So configured, the area of the fabric comprising the pleat 22 may measure approximately 200 square inches. However, in other illustrative embodiments of the surgical drape 10 the pleats 22 may be differently configured, having either a different height or width, which may result in an area of fabric greater than 200 square inches or less than 200 square inches without limitation unless otherwise indicated in the following claims. It is contemplated that the optimal configuration, dimensions, area, etc. of the pleats 22 may vary from one application of the surgical drape 10 to the next, and that for many applications a height (i.e., the dimension parallel to the right and left edges 13, 15) may be between 4 inches and 30 inches and a width between 6 inches and 30 inches (and, consequently, an area of fabric comprising the pleat 22 of between 20 square inches and 320 square inches) may especially advantageous, again without limitation unless otherwise indicated in the following claims. In other illustrative embodiments the area of material comprising the pleat 20 may be 24, 30, 36, 42, 48, 54, 60, 66, 72, 78, 84, 90, 96, 102, 108, 114, 120, 126, 12, 138, 144, 150, 156, 162, 168, 174, 180, 186, 192, 198, 204, 210, 216, 222, 228, 234, 240, 246, 252, 258, 264, 270, 276, 282, 288, 294, 300, 306, 312, or 318 square inches. Generally, the armboard covers 20 and pleats 22 may be configured such that during an anterior approach hip surgical procedure, both the patient's 5 arms may be extended outward 90 degrees from the patient's 5 body (e.g., in a position the same as or similar to that shown in FIGS. 1A & 1B) and medical personnel (e.g., an anesthetist, anesthesiologist, etc.) may access the patient's 5 arms simultaneously without entering and/or compromising the sterile field.

Generally, the various portions of the surgical drape 10 may be separately formed and then engaged with one another (via any suitable method and/or apparatus, including but not limited to sewing, chemical adhesives, etc. unless otherwise indicated in the following claims) or formed integrally with one another. Accordingly, the scope of the present disclosure is not limited by whether one or both armboard covers 20, pleats 22, etc. are integrally formed with the main portion of the surgical drape 10 or if one or both armboard covers 20, pleats 22, etc. are separately formed therefrom and later engaged with the main portion of the surgical drape 10 unless otherwise indicated in the following claims.

Although the surgical drape 10 and method for using same are described herein with reference to a patient positioning table 8 configured as a Hana® Table, the scope of the surgical drape 10 and/or method of using same is not so limited unless otherwise indicated in the following claims. Additionally, although the surgical drape 10 and method for using same are described herein with reference to an anterior approach hip surgical procedure, and with special emphasis on an anterior approach total hip replacement procedure, the surgical drape 10 may be used for any procedure for which the surgical drape 10 is suited without limitation unless otherwise indicated in the following claims. Accordingly, the scope of the present disclosure extends to any beneficial and/or advantageous feature of the surgical drape 10 and/or use thereof without limitation unless so indicated in the following claims.

The materials used to construct the various apparatuses disclosed herein may vary depending on the specific application thereof, but it is contemplated that for many applications it may be advantageous to construct the surgical drape 10 of a material that is impervious to blood and/or other body fluids, which material may be comprised of polymers, synthetic materials, metals, metal alloys, natural materials, and/or combinations thereof without limitation unless otherwise indicated in the following claims. Additionally, for certain applications it may be advantageous for the surgical drape 10 to be comprised of a fabric or textile that is either woven or non-woven, depending at least upon the specific material selected and without limitation unless otherwise indicated in the following claims. Accordingly, the above-referenced elements may be constructed of any material known to those skilled in the art or later developed, which material is appropriate for the specific application of the present disclosure without departing from the spirit and scope of the present disclosure unless so indicated in the following claims.

Having described preferred aspects of the various processes and apparatuses, other features of the present disclosure will undoubtedly occur to those versed in the art, as will numerous modifications and alterations in the embodiments and/or aspects as illustrated herein, all of which may be achieved without departing from the spirit and scope of the present disclosure. Accordingly, the methods and embodiments pictured and described herein are for illustrative purposes only, and the scope of the present disclosure extends to all processes, apparatuses, and/or structures for providing the various benefits and/or features of the present disclosure unless so indicated in the following claims.

While the apparatuses and methods of the present disclosure have been described in connection with preferred aspects and specific examples, it is not intended that the scope be limited to the particular embodiments and/or aspects set forth, as the embodiments and/or aspects herein are intended in all respects to be illustrative rather than restrictive. Accordingly, the apparatuses, processes, and illustrative embodiments pictured and described herein are no way limiting to the scope of the present disclosure unless so stated in the following claims.

Although several figures are drawn to accurate scale, any dimensions provided herein are for illustrative purposes only and in no way limit the scope of the present disclosure unless so indicated in the following claims. It should be noted that the apparatuses and methods are not limited to the specific embodiments pictured and described herein, but rather the scope of the inventive features according to the present disclosure is defined by the claims herein. Modifications and alterations from the described embodiments will occur to those skilled in the art without departure from the spirit and scope of the present disclosure.

Any of the various features, components, functionalities, advantages, aspects, configurations, process steps, process parameters, etc. of the apparatuses and methods disclosed herein may be used alone or in combination with one another depending on the compatibility of the features, components, functionalities, advantages, aspects, configurations, process steps, process parameters, etc. Accordingly, a nearly infinite number of variations of the present disclosure exist. Modifications and/or substitutions of one feature, component, functionality, aspect, configuration, process step, process parameter, etc. for another in no way limit the scope of the present disclosure unless so indicated in the following claims.

It is understood that the present disclosure extends to all alternative combinations of one or more of the individual features mentioned, evident from the text and/or drawings, and/or inherently disclosed. All of these different combinations constitute various alternative aspects of the present disclosure and/or components thereof. The embodiments described herein explain the best modes known for practicing the apparatuses, methods, and/or components disclosed herein and will enable others skilled in the art to utilize the same. The claims are to be construed to include alternative embodiments to the extent permitted by the prior art.

Unless otherwise expressly stated in the claims, it is in no way intended that any process or method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including but not limited to: matters of logic with respect to arrangement of steps or operational flow; plain meaning derived from grammatical organization or punctuation; the number or type of embodiments described in the specification.

What is claimed:

1. A surgical drape comprising:
   a. a head end, wherein said head end is positioned adjacent a patient's head during use;
   b. a bar end, wherein said bar end is positioned adjacent a patient's feet during use;
   c. a length between 140 and 180 inches, wherein said length is defined as extending from a terminal edge of said head end to a terminal edge of said bar end;
   d. a left edge generally perpendicular to both said terminal edge of said bar end and said terminal edge of said head end;

e. a right edge generally perpendicular to both said terminal edge of said bar end and said terminal edge of said head end, wherein said right edge and said left edge are generally parallel with respect to one another;
f. a width between 102 and 126 inches, wherein said width is defined as extending from a terminal edge of said left edge to a terminal edge of said right edge;
g. an aperture positioned between said head end and said bar end and between said left edge and said right edge, wherein said aperture is centered between said left edge and said right edge, and wherein said aperture extends through said surgical drape;
h. a first armboard cover positioned adjacent said head end and said right edge, wherein said armboard cover extends outward from said right edge by a distance of between 8 and 20 inches; and,
i. a second armboard cover positioned adjacent said head end and said left edge, wherein said armboard cover extends outward from said left edge by a distance of between 8 and 20 inches;
j. a first pleat formed adjacent said first armboard cover; and,
k. a second pleat formed adjacent said second armboard cover, wherein said head end, said bar end, said left edge, said right edge, said first armboard cover, said second armboard cover, said first pleat, and said second pleat are integrally formed with one another as constructed of a single piece of material.

2. The surgical drape according to claim 1 wherein said aperture is further defined as being rectangular in shape.

3. The surgical drape according to claim 2 wherein said aperture is further defined as having an area of between 64 and 324 square inches.

4. The surgical drape according to claim 1 wherein said aperture is further defined as being rectangular in shape.

5. The surgical drape according to claim 1 wherein said surgical drape further comprises a barrier drape positioned adjacent said aperture.

6. The surgical drape according to claim 1 wherein an area of a material comprising said first pleat is between 48 and 300 square inches.

7. The surgical drape according to claim 6 wherein said first and second pleats are further defined as being symmetrical about a length of said surgical drape from said head end to said bar end.

8. A method of creating a sterile field, said method comprising:
  a. positioning a patient on a patient positioning table such that an anterior portion of said patient is facing upward;
  b. extending a first arm of said patient away from a torso of said patient;
  c. extending a second arm of said patient away from said torso of said patient;
  d. extending a first leg of said patient;
  e. extending a second leg of said patient;
  f. covering a portion of said patient with a surgical drape, wherein said portion includes the entirety of said patient except for a second portion that is exposed via an aperture formed in said surgical drape, said surgical drape comprising:
    i. a head end, wherein said head end is positioned adjacent a head of said patient;
    ii. a bar end, wherein said bar end is positioned adjacent a foot of said patient;
    iii. a length between 140 and 180 inches, wherein said length is defined as extending from a terminal edge of said head end to a terminal edge of said bar end;
    iv. a left edge generally perpendicular to both said terminal edge of said bar end and said terminal edge of said head end;
    v. a right edge generally perpendicular to both said terminal edge of said bar end and said terminal edge of said head end, wherein said right edge and said left edge are generally parallel with respect to one another;
    vi. a width between 102 and 126 inches, wherein said width is defined as extending from a terminal edge of said left edge to a terminal edge of said right edge;
    vii. said aperture positioned between said head end and said bar end and between said left edge and said right edge, wherein said aperture is centered between said left edge and said right edge, and wherein said aperture extends through said surgical drape;
    viii. a first armboard cover positioned adjacent said head end and said right edge, wherein said armboard cover extends outward from said right edge by a distance of between 8 and 20 inches;
    ix. a second armboard cover positioned adjacent said head end and said left edge, wherein said armboard cover extends outward from said left edge by a distance of between 8 and 20 inches;
    x. a first pleat formed adjacent said first armboard cover; and,
    xi. a second pleat formed adjacent said second armboard cover, wherein said head end, said bar end, said left edge, said right edge, said first armboard cover, said second armboard cover, said first pleat, and said second pleat are integrally formed with one another as constructed of a single piece of material; and,
  g. positioning said aperture over said second portion of said patient.

9. The method according to claim 8 further comprising the step of allowing a medical personnel to access said right arm of said patient without said medical personnel entering said sterile field.

10. The method according to claim 9 further comprising the step of allowing said medical personnel to access said left arm of said patient without said medical personnel entering said sterile field.

11. The method according to claim 10 further comprising the step of allowing said medical personnel to access a control of said patient positioning table adjacent said bar end of said surgical drape without said medical personnel entering said sterile field.

12. The method according to claim 11 further comprising the step of allowing said medical personnel to access said head of said patient adjacent said head end of said surgical drape without said medical personnel entering said sterile field.

13. The method according to claim 8 wherein said surgical drape further comprises a barrier drape engaged with said surgical drape adjacent said aperture.

14. The method according to claim 8 wherein said aperture is further defined as being rectangular in shape.

15. The method according to claim 14 wherein said aperture is further defined as having an area of between 64 and 324 square inches.

16. The method according to claim 8 wherein said aperture is further defined as being rectangular in shape.

17. The method according to claim 8 wherein an area of a material comprising said first pleat is between 48 and 300 square inches.

18. The method according to claim 17 wherein said first and second pleats are further defined as being symmetrical about a length of said surgical drape from said head end to said bar end.

\* \* \* \* \*